(12) United States Patent
Higuchi et al.

(10) Patent No.: US 6,375,641 B2
(45) Date of Patent: *Apr. 23, 2002

(54) MEDICAL ANESTHETIC NEEDLE

(75) Inventors: Akio Higuchi; Hayato Hyugaji, both of Tokyo (JP)

(73) Assignee: Dr. Japan Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/091,915
(22) PCT Filed: Oct. 1, 1997
(86) PCT No.: PCT/JP97/03497
  § 371 Date: Jun. 25, 1998
  § 102(e) Date: Jun. 25, 1998
(87) PCT Pub. No.: WO99/16486
  PCT Pub. Date: Apr. 8, 1999
(51) Int. Cl.[7] .................................. A61M 5/32
(52) U.S. Cl. .................. 604/272; 604/158; 604/164.01; 604/164.06; 604/264; 604/198
(58) Field of Search ................ 604/164, 168, 604/110, 158, 192, 195, 196, 198, 263–4, 167, 164.01, 164.06, 272, 44; 600/564

(56) References Cited

U.S. PATENT DOCUMENTS 4,693,257 A * 9/1987 Markham .................. 128/752
4,926,877 A * 5/1990 Bookwalter ................ 128/754
5,263,937 A * 11/1993 Shipp ......................... 604/164
5,397,512 A * 3/1995 Sloane, Jr. et al. ........... 264/25
5,470,318 A * 11/1995 Griffith, III et al. ........ 604/161
5,601,603 A * 2/1997 Illi ............................. 604/213
5,630,802 A * 5/1997 Moellmann et al. ........ 604/164

FOREIGN PATENT DOCUMENTS

WO    WO-95/17126 A1 * 6/1995 ........... A61B/10/00

* cited by examiner

*Primary Examiner*—Glenn K. Dawson
*Assistant Examiner*—Jennifer Maynard
(74) *Attorney, Agent, or Firm*—Birch, Stewart, Kolasch & Birch, LLP

(57) ABSTRACT

A medical anesthetic needle (1) is provided that includes an inner needle (3) of a straight needle shape, having a pencil-pointed tip (4), and an outer needle (2) of a straight tubular shape, having the inner needle inserted thereinto and therethrough from the rear end thereof. A foremost-end part (12) of a hollow, truncated conical shape or the like of the outer needle (2) is formed so that the minimum inner diameter thereof is smaller than the outer diameter of the main body (5) of the inner needle (3). When the inner needle (3) is inserted into and through the outer needle (2), the circumferential fore-end edge of the foremost-end part (12) is in close contact with the circumferential surface of the tip (4) or the main body (5) of the inner needle (3), and no gaps are thus formed therebetween. Therefore, when needled, a patient's nervous tissue is unlikely to be nipped in a gap between the inner and outer needles to cause pain to the patient.

2 Claims, 3 Drawing Sheets

US 6,375,641 B2

MEDICAL ANESTHETIC NEEDLE

This application claims the benefit under 35 U.S.C. §371 of prior PCT International Application No. PCT/JP97/03497 which has an International filing date of Oct. 1, 1997 which designated the United States of America, the entire contents of which are hereby incorporated by reference.

TECHNICAL FIELD

The present invention relates to a medical anesthetic needle including an inner needle, having a pencil-pointed tip, and a tubular outer needle, having the inner needle inserted thereinto and therethrough.

BACKGROUND TECHNOLOGY

Conventional inner needles, having a pencil-pointed tip (4), of anesthetic needles, are inserted into and through a straight-tubular outer needle having its fore-end section formed in a tapered shape, tapering off towards the end thereof, i.e., a hollow, truncated conical shape. The fore-end part of the outer needle was deburred, but relatively sharp, thus resulting in patients often feeling pain when the needle is inserted into the body. An anesthetic needle for easing such pain is disclosed in Japanese Utility Model No. 3018360 where the fore-end section of a tubular outer needle has the edge formed to be round on the right-angled cut fore-end face thereof.

With an anesthetic needle with the fore-end section of a tubular outer needle thereof having the edge formed to be round on the right-angled cut fore-end face, the patient's pain when pricked with the needle was eased somewhat in comparison with an anesthetic needle having a sharp-edged fore-end section of its tubular outer needle. However, the extent of its pain reduction was not enough.

The cause of a patient feeling pain when pricked with a needle, even though the fore-end part of the tubular outer needle is formed to be round, is the presence of a gap between the fore-end section of the outer needle and the inner needle. The difference between the outer diameter of the inner needle and the inner diameter of the outer needle is about 0.05 to 0.1 mm, depending on the needle size. Thus, a gap having a maximum width of 0.05 to 0.1 mm may be formed since the inner needle tends to be decentered relative to the outer needle when needling. When a patient's nervous tissue is nipped in this gap, the patient feels pain.

DISCLOSURE OF THE INVENTION

An object of the present invention is to provide a medical anesthetic needle including an inner needle having a straight needle shape, and a pencil-pointed tip, and having an outer needle with a straight tubular shape, having the inner needle inserted thereinto and therethrough, wherein the medical anesthetic needle is capable of sufficiently easing the enough a patient's pain when needled.

To accomplish this object, a medical anesthetic needle, is provided, which includes an inner needle with a straight needle shape and a pencil-pointed tip, and an outer needle with a straight tubular shape and having the inner needle inserted thereinto and therethrough, wherein the fore-end part of the outer needle is formed in a tapered shape, tapering off towards the end thereof, i.e., a hollow, truncated conical shape or the like. Furthermore, the foremost section of the fore-end part is formed as a foremost-end part so that the minimum inner diameter of the foremost-end part is smaller than the outer diameter of a section of the inner needle excluding the tip, i.e., the main body of the inner needle.

The foremost-end part of the outer needle may be applied only with deburring so that the edge of its right-angled cut fore-end face is left sharp. If required, the foremost-end part may have the edge of its right-angled cut fore-end face worked to be round.

With an anesthetic needle of the present invention, when a patient is pricked with a needle, the foremost-end part of its outer needle is located on the circumferential surface of either a section near the root of the tip or the main body of the inner needle where the outer diameter of the inner needle is equal to or greater than the minimum inner diameter of the foremost-end part of the outer needle. Thus, no gaps, are formed at all between the foremost-end part of the outer needle and the inner needle. Therefore, the patient is not likely at all to feel pain caused by the patient's nervous tissue being nipped between the outer and inner needles.

BRIEF DESCRIPTION OF THE DRAWINGS

The present invention will become more fully understood from the detailed description given hereinbelow and the accompanying drawings which are given by way of illustration only, and thus are not imitative of the present invention, and wherein.

DETAILED DESCRIPTION OF THE INVENTION

Figure 1:
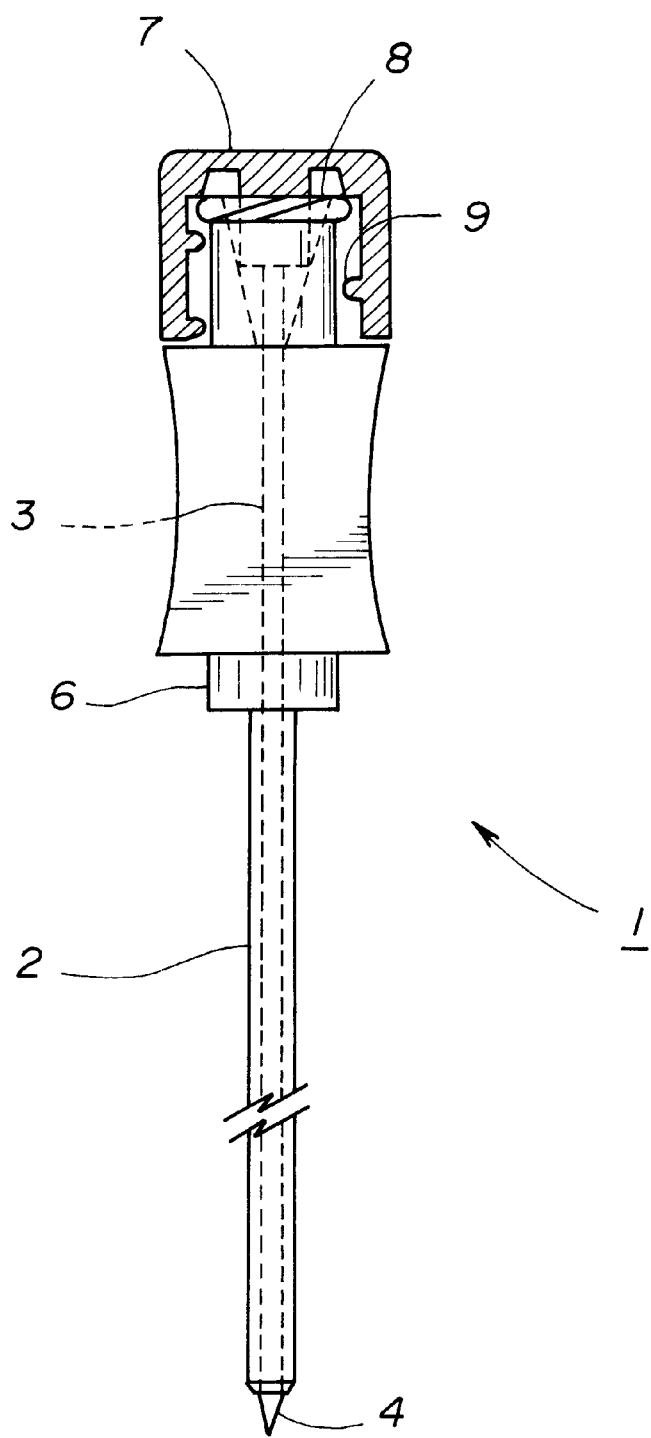
FIG. 1 is a plan view showing an external appearance of a medical anesthetic needle according to one embodiment of the present invention.

As shown in FIG. 1, an anesthetic needle 1 includes a hollow outer needle 2 made of stainless steel tube and a solid inner needle 3 made of stainless steel bar. The rear end of the outer needle 2 is fixed to a needle base 6. The inner needle 3 is inserted through a needle hole of the needle base 6 into the outer needle 2. A tip 4 of the inner needle 3 that protrudes from the end of the outer needle 2 is of a pencil-pointed shape, i.e., a conical shape. A cap 7 is fixed to the rear end of the inner needle 3, where a spiral-shaped female screw part 9 is formed on the internal circumferential surface of the cap 7. A spiral-shaped male screw part 8 that engages with the female screw part 9 of the cap 7, is disposed on a section protruding from the rear end of the needle base 6. When inserting the anesthetic needle, the male screw part 8 is screwed into the female screw part 9 to its limit, to define the axial limit position of the inner needle 3 relative to the outer needle 2.

Figure 2:
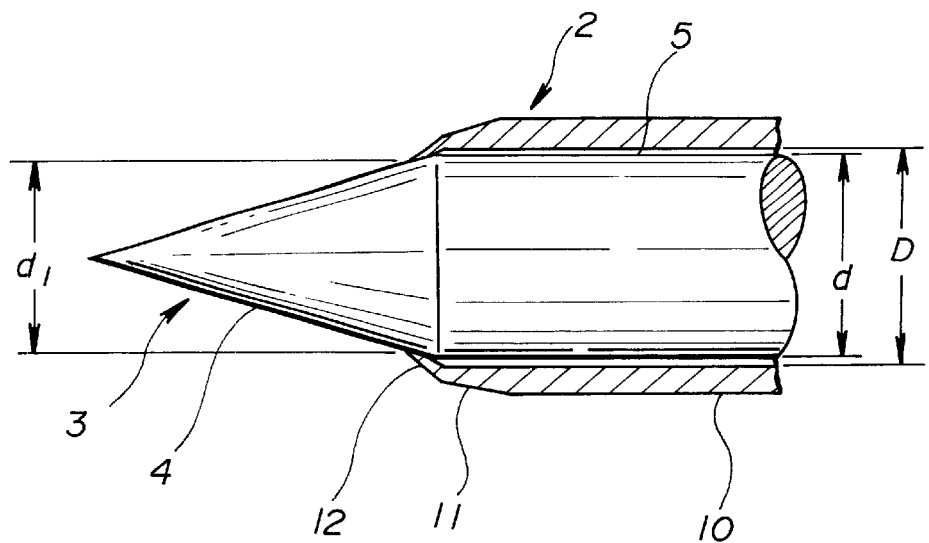
FIG. 2 is a longitudinal sectional view showing the fore-end section of the medical anesthetic needle of FIG. 1, as enlarged.

As shown in FIG. 2, the inner needle 3 includes a main body 5 of a round-column shape having a diameter d, and the tip 4 of a conical shape protruding axially from the main body 5 towards the fore-end side thereof. The outer needle 2 includes a main body 10 of a round cylindrical shape having an inner diameter D slightly greater than the diameter d of the main body 5 of the inner needle; a fore-end part 11 having a tapered shape tapering off and extending towards the fore-end side thereof, i.e., a hollow, truncated conical shape, and a foremost-end part 12 having a tapered shape which further tapers off and extends from the fore-end part 11 towards the fore-end side thereof, i.e., a hollow, truncated conical shape. While the inner diameter of the fore-end part 11 is constant and equal to the inner diameter of the main body 10, the inner diameter of the foremost-end part 12 is gradually reduced along the axis thereof towards the fore-end side thereof with the minimum inner diameter thereof being slightly smaller than the outer diameter d of the main body 5 of the inner needle. While the outer diameter of the fore-end part 11 is equal to the outer diameter of the main body 10 at the joining section thereof with the main body 10, the outer diameter is continuously reduced from this section towards the fore-end side. While the outer diameter of the foremost-end part 12 is equal to the outer diameter of the fore-end part 11 at the joining section thereof with the fore-end part 11, the outer diameter is continuously reduced from that section towards the fore-end side, and is equal to the inner diameter at the foremost-end. The axial length of the foremost-end part 12 is smaller the axial length of the fore-end part 11. The inclination angle of the internal circumferential conical surface of the foremost-end part 12 is equal to or slightly, greater than the inclination angle of the conical surface of the tip 4 of the inner needle 3.

FIGS. 1 and 2 show a state of the female screw part 9 of the cap 7 being screwed onto the male screw part 8 of the needle base 6 to the maximum limit, i.e., the state of the anesthetic needle 1 when needling, where the foremost-end part 12 is located on the circumferential surface, having an outer diameter $d_1$, of the tip 4 of the inner needle 3. Although the outer diameter $d_1$ is smaller than the outer diameter d of the main body 5 of the inner needle, the outer diameter $d_1$ is equal to or greater than the minimum inner diameter $D_1$, which will be described later, of the foremost-end part 12 of the outer needle. Therefore, the circumferential fore-end edge of the foremost-end part 12, having an inner diameter equal to the minimum inner diameter, comes in close contact with the entire circumferential surface near the root of the tip 4, having the diameter $d_1$, with the circumferential fore-end edge either being kept as it is or elastically expanded. As a result, no gaps are formed between the circumferential surface of the tip 4 and the foremost-end part 12.

Figure 3:
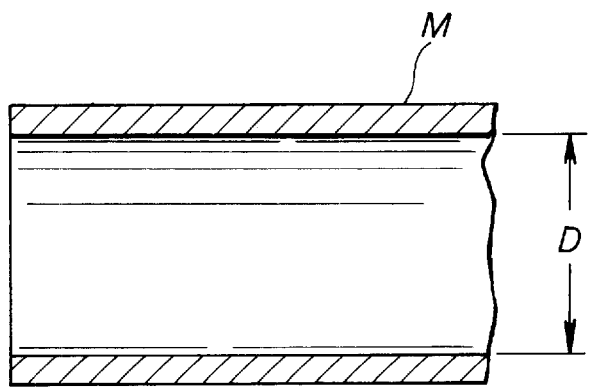
FIG. 3 is a view showing a working process for the fore-end section of the outer needle of FIG. 2.
Figure 3:
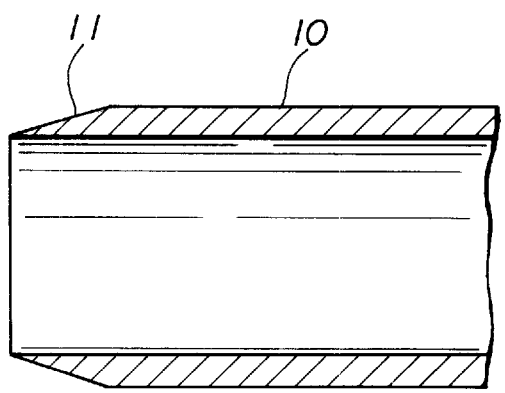
Figure 3:
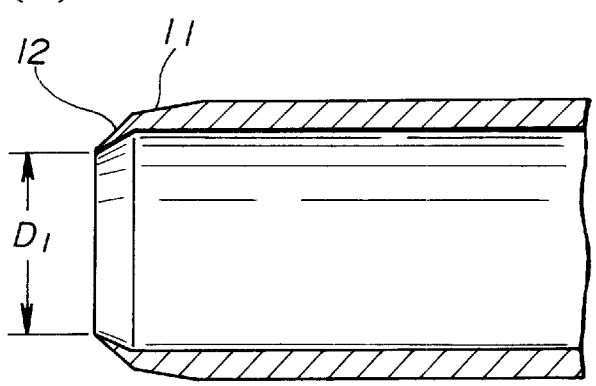

FIG. 3 is a view showing a process of forming the fore-end part 11 and the foremost-end part 12 of the outer needle 2. The corner of a fore-end part of a stainless steel tube M having an inner diameter D, as shown in FIG. 3(a), is machine-cut to form a main body 10 of a hollow, round cylindrical shape and a sharp-edged fore-end part 11 of a hollow, truncated conical shape, as shown in FIG. 3(b). At this time, the burr caused on the foremost end is removed by grinding. If required, the foremost end is finished so that the foremost end is round in a sectional plane containing the axis. Next, as shown in FIG. 3(c), the foremost-end section of the fore-end part 11 is roll-worked by squeezing so that the minimum inner diameter $D_1$ is obtained that is smaller than the outer diameter of the main body of the inner needle, thereby forming the foremost-end part 12 of a hollow, truncated conical shape.

When a patient is needled with the anesthetic needle of FIG. 2, the internal circumferential fore-end edge of the foremost-end part 12 of the outer needle 2 comes in close contact with the circumferential surface, on the entire circumference thereof, of the conical-shaped tip 4 of the inner needle 3, and no gaps are thus formed between the foremost-end part 12 of the outer needle 2 and the tip 4 of the inner needle 3; therefore, the patient's nervous tissue is not likely at all to be nipped in a gap therebetween to cause any particular pain to the patient.

Although the anesthetic needle of FIG. 2 is arranged such that the foremost-end part 12 of the outer needle 2 is located on the tip 4 when the cap at the rear end of the inner needle is engaged with the needle base at the rear end of the outer needle, it also can be arranged such that the foremost-end part 12 of the outer needle 2 is located not on the tip 4 but on the main body 5, positioned behind the tip 4, of the inner needle 3 when the cap at the rear end of the inner needle is fully engaged to the limit with the needle base at the rear end of the outer needle so as to keep the inner needle from coming out of the outer needle.

Figure 4:
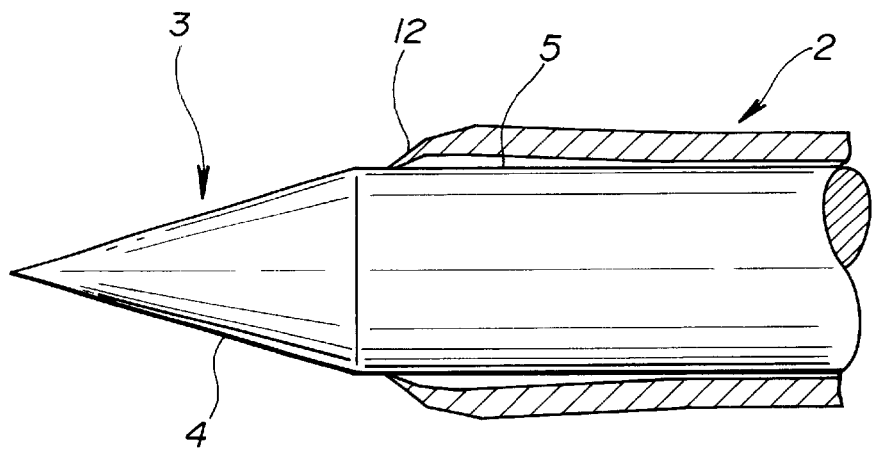
FIG. 4 is a view corresponding to FIG. 2, showing another embodiment of the present invention.

With the anesthetic needle as shown in FIG. 4, when needling, since the fore-end section of the outer needle 2 has its inner diameter expanded due to elastic deformation, and the circumferential fore-end edge of the foremost-end part 12 comes in close contact with the circumferential surface of the main body 5 of the inner needle 3, due to the resilience, no gaps are formed at all between the foremost-end part 12 and the inner needle 3. Therefore, similarly to the embodiment described earlier, the patient's nervous tissue is not likely to be nipped in a gap between the outer needle 2 and inner needle 3, whereby the patient cannot feel such any particular pain by any means.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A medical anesthetic needle comprising an inner needle main body having a pencil-pointed, conically shaped tip and an outer needle having a straight tubular shape, the inner needle being inserted into and through the tubular outer needle from the rear end thereof, wherein said outer needle includes:

an outer needle main body with a hollow, cylindrical shape having an inner diameter (D) greater than an outer diameter (d) of said inner needle main body, said outer needle having a fore-end portion, a foremost-end portion and a rear end portion, said fore-end portion having a hollow, truncated, substantially conical shape that extends axially from said outer needle main body towards the fore-end portion of said outer needle; and the foremost-end portion having a hollow, truncated substantially conical shape that further extends axially from said fore-end portion towards the fore-end side of said outer needle;

wherein, when the inner diameter of said fore-end portion is constant and equal to the inner diameter of said outer needle main body, the inner diameter of said foremost-end portion is reduced along the axis thereof towards the fore-end thereof with the minimum inner diameter ($d_1$) of said foremost-end portion being smaller than the outer diameter (d) of said main body of said inner needle, said foremost-end portion having a circumferential fore-end edge which is biased against a circumferential surface of said tip of said inner needle when said inner needle is inserted into and through said outer needle to its limit, whereby a smooth transition is created between the circumferential fore-end edge of the tubular outer needle and the circumferential surface of the conically shaped tip of the inner needle.

2. The medical anesthetic needle of claim 1, wherein the inner needle main body and the outer needle main body define a space therebetween which is substantially constant along its entire length.

* * * * *